United States Patent [19]

Mori et al.

[11] Patent Number: 4,843,530

[45] Date of Patent: Jun. 27, 1989

[54] LIGHT RAY RADIATION STAND

[75] Inventors: Kei Mori; Kazuyoshi Hara, both of Tokyo, Japan

[73] Assignee: Kei Mori, Tokyo, Japan

[21] Appl. No.: 181,888

[22] Filed: Apr. 15, 1988

[30] Foreign Application Priority Data

Dec. 28, 1987 [JP] Japan .......................... 62-199831[U]

[51] Int. Cl.$^4$ .............................. F21S 1/12; F21V 8/00
[52] U.S. Cl. ...................................... 362/413; 362/32;
362/419; 362/422; 362/430
[58] Field of Search ................. 362/32, 391, 413, 419,
362/422, 424, 426, 430; 358/91

[56] References Cited

U.S. PATENT DOCUMENTS

| 866,473 | 9/1907 | Keefe et al. | 362/391 |
| 1,340,108 | 5/1920 | Blasco | 362/419 |
| 3,564,231 | 2/1971 | Bruce et al. | 362/32 |
| 3,766,374 | 5/1973 | Fairchild | 362/32 |
| 3,923,372 | 12/1975 | Roland | 362/32 |
| 4,385,344 | 5/1983 | Gonser | 362/32 |
| 4,449,171 | 5/1984 | Warshawsky | 362/422 |
| 4,477,865 | 10/1984 | Tsuyama | 362/396 |
| 4,605,990 | 8/1986 | Wilder et al. | 362/32 |
| 4,782,430 | 11/1988 | Robbins et al. | 362/32 |

FOREIGN PATENT DOCUMENTS

| 866273 | 3/1940 | France | 362/424 |
| 1141552 | 1/1956 | France | 362/424 |
| 2117131 | 10/1983 | United Kingdom | 362/32 |

*Primary Examiner*—Ira S. Lazarus
*Assistant Examiner*—David G. Messer
*Attorney, Agent, or Firm*—Jordan and Hamburg

[57] ABSTRACT

A light ray radiation stand comprises a foundation, one or more deformable flexible conduits vertically installed on the upper part of the foundation and an optical conductor cable holding means mounted on the tip end portion of each conduit. The optical conductor cable transmits the light rays therethrough and emits the same from the end portion.

7 Claims, 6 Drawing Sheets

LIGHT RAY RADIATION STAND

BACKGROUND OF THE INVENTION

The present invention relates to a light ray radiation stand, in particular, a light ray radiation stand capable of holding optical conductor cables which can transmit light rays in an optional desired direction.

In recent years, a large number of persons suffer from incurable diseases such as arthritis, neuralgia and rheumatism, or pain from injuries, bone fractures or from ill-defined diseases. Furthermore, persons cannot avoid growing old and of their skin aging which progresses gradually from a comparatively young age. On the other hand, the present applicant has previously proposed to focus the sun's rays or artificial light rays by the use of lenses or the like, to guide the same into an optical conductor cable, and to transmit them onto an optional desired place through the optical conductor cable. Those light rays transmitted in such a way are employed for use in illumination or for other like purposes as for example to cultivate plants, chlorella or the like. In the process, it has been found that visible light rays not containing therein ultraviolet rays, infrared rays etc. promote a living body reaction, and thereby the same promote the health of persons or prevent people's skin from showing the effects of growing old. Furthermore, there are the noticeable beneficial effects of recovering from arthritis, neuralgia, bedsores, rheumatism, burns, skin diseases, injuries, bone fractures, or the like, and of relieving pain from those diseases. Such beneficial effects have been witnessed by the present applicant.

And further, on the basis of the inventor's discovery, the applicant has previously proposed a light ray radiation device for administering various types of medical treatments and beauty treatments and for promoting the general health of a person.

The light ray radiation device for use in medical treatment previously proposed by the present applicant has an optical conductor cable. At the end portion thereof, the sun's rays or artificial light rays are guided into it, and transmitted therethrough. The light rays i.e. the white-colored light rays corresponding to the visible light ray components of the sun's rays, are transmitted through the optical conductor cable as was previously proposed by the present applicant in various ways. A hood member is installed at the light-emitting end portion of the optical conductor cable. At the time of administering medical treatment, a patient is placed in a chair and the light rays, consisting of the visible light ray components, are transmitted through the optical conductor cable in the manner mentioned above, are radiated onto the diseased part of a patient.

As mentioned above, the light rays to be radiated onto the diseased part of the patient are the ones corresponding to the visible light ray components of the sun's rays and therefore contain therein neither ultraviolet rays nor infrared rays. Consequently, it may be possible to administer medical treatment safely. However, the above-mentioned light ray radiation device for use in medical treatment is large-scaled and consequently very expensive. In the case of employing such a device in a family setting, the cost would be prohibitive. Furthermore, the usual device would need much space. Those are the problems to be solved.

SUMMARY OF THE INVENTION

It is an object of the present invention to provide a light ray radiation stand capable of radiating the light rays transmitted through an optical conductor cable in an optional desired direction.

It is another object of the present invention to provide a light ray radiation stand which can be preferably employed in a family setting.

It is another object of the present invention to provide a light ray radiation stand which is low-cost; which is capable of being easily transported around; which doesn't need much space, and which can radiate the light rays in an optional desired direction and thereby can be used very readily.

DESCRIPTION OF THE PREFERRED EMBODIMENTS

Figure 1:
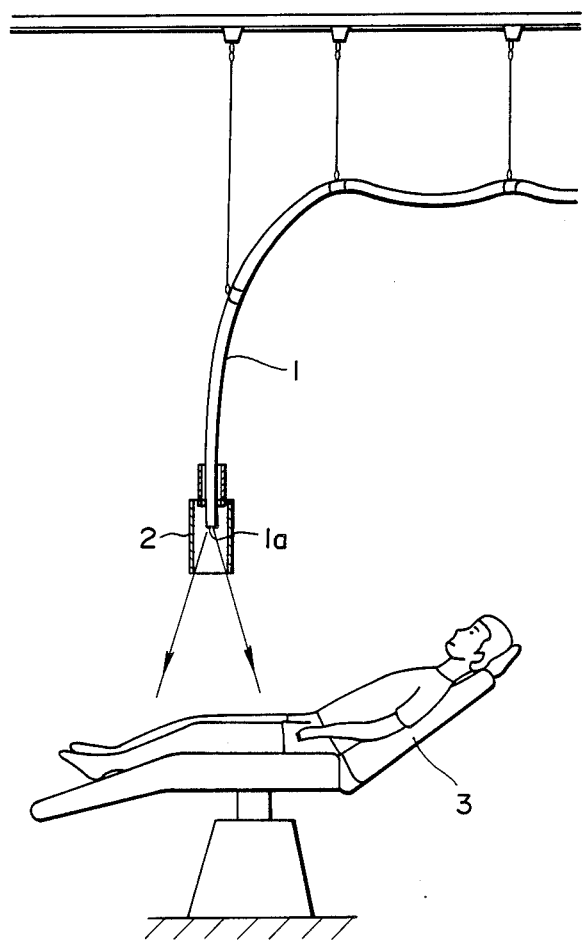
FIG. 1 is a view for explaining an embodiment of a light ray radiation device for use in medical treatment as previously proposed by the present applicant.

FIG. 1 is a construction view for explaining an embodiment of the light ray radiation device for use in medical treatment as previously proposed by the present applicant. In FIG. 1, 1 is an optical conductor cable. At the end portion thereof, not shown in FIG. 1, the sun's rays or artificial light rays are guided into it, and transmitted therethrough. The light rays i.e. the white-colored light rays corresponding to the visible light ray components of the sun's rays, are transmitted through the optical conductor cable as was previously proposed by the present applicant in various ways. In FIG. 1, 2 is a hood member installed at the light-emitting end portion 1a of the optical conductor cable 1, and 3 is a chair for use in medical treatment. At the time of administering medical treatment, a patient is placed in the chair 3 and the light rays, consisting of the visible light ray components, transmitted through the optical conductor cable 1 in the manner mentioned above, are radiated onto the diseased part of the patient.

As mentioned above, the light rays to be radiated onto the diseased part of the patient are the ones corresponding to the visible light ray components of the sun's rays and therefore contain therein neither ultraviolet rays nor infrared rays. Consequently, it may be possible to administer medical treatment safely. However, the above-mentioned light ray radiation device for use in medical treatment is large-scaled and consequently very expensive. In the case of employing such a device in a family setting, the cost would be prohibitive. Furthermore, the usual device would need much space. Those are the problems to be solved.

Figure 2A:
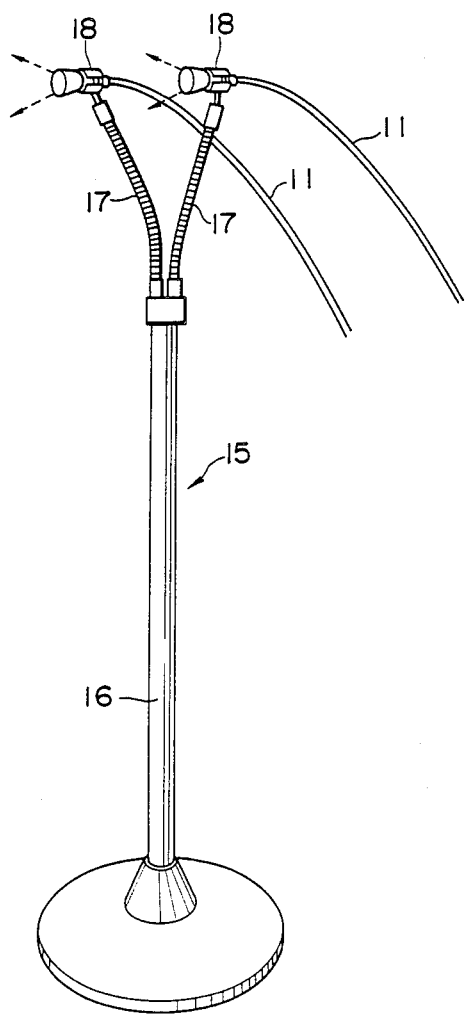
FIGS. 2(a) and 2(b) represent an entire perspective view for explaining an embodiment of a light ray radiation stand according to the present invention.
Figure 2B:
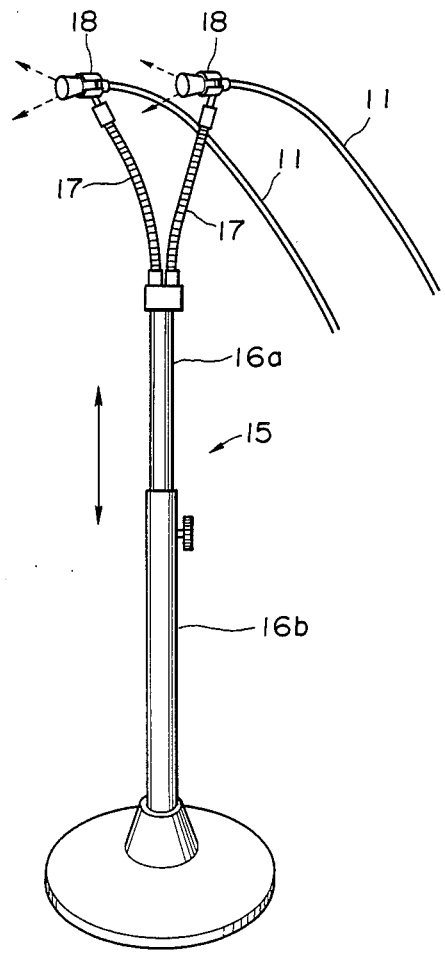

FIGS. 2(a) and 2(b) are perspective views for explaining embodiments for light ray radiation stands according to the present invention. In FIG. 2(a), 11 is an optical conductor cable for transmitting therethrough the sun's rays collected by means of a sun ray collecting device not shown in FIG. 2(a) and 15 is a light ray radiation stand according to the present invention.

The light ray radiation stand 15 comprises a foundation 16, one or more deformable flexible conduits 17 vertically installed on the foundation 16, and a supporter 18 mounted on the end portion of the conduit 17 and used for detachably supporting the optical conductor cable 11. At the time of employing the light ray radiation device, the end portion of the optical conductor cable 11 is supported by the supporter 18.

According to the afore-mentioned present invention, since the conduit 17 can be freely deformed and kept in that condition, the radiation from the optical conductor cable 11 can be bent in an optional desired direction. Therefore, the light ray radiation stand of the present invention can be easily utilized. Furthermore, when the stand is not being used, the optical conductor cable 11 is removed from the stand, and the stand can be put back into a conveniently small space.

In the other embodiment shown in FIG. 2(b), the foundation 16 is divided into two portions 16a and 16b. The portion 16b is comprised of a pipe member and the portion 16a is inserted into the pipe section 16b in order to be able to adjust the height of the stand by sliding up and down the portion 16a inside the portion 16b.

Figure 3:
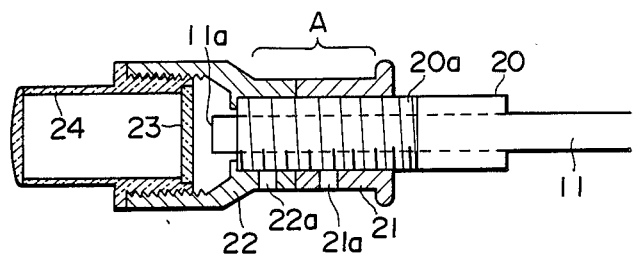
FIG. 3 is a detailed cross-sectional view for explaining the light-emitting end side of the optical conductor cable.

FIG. 3 is a cross-sectional view for explaining an embodiment of the end portion (the light-emitting end) of the optical conductor cable 11 shown in FIGS. 2(a) and 2(b). In FIG. 3, 11 is an optical conductor cable, 11a the light-emitting end of the optical conductor cable 11, 20 an external cover attached to the light-emitting end of the optical conductor cable 11, 21 a nut, 22 a connector, 23 a heat-reflecting filter, and 24 a transparent cap. The nut 21 and the connector 22 are engaged by a screw portion 20a formed on the external circumferential portion of the external covering 20 as shown in FIG. 3. After being engaged therewith, a tool fitted to a hole of a special shape is inserted into the holes of a similar shape 21a and 22a which are respectively bored into the nut 21 and the connector 22, and thereby the nut 21 and the connector 22 are firmly fastened opposite to each other. In such a way, the nut 21 and the connector 22 are firmly fixed onto the end portion of the optical conductor cable 11. After fixing the nut 21 and the connector 22 thereon, both of them cannot be detached from the optical conductor cable 11 without using the afore-mentioned special tool, and thereby its safety can be guaranteed. In such a way, after fixing the connector 22 on the end portion of the optical conductor cable 11, the transparent cap 24 is attached to the connector 22 through the heat-reflective filter 23 as the occasion demands. The light rays emitted from the end portion 11a of the optical conductor cable 11 are transmitted through the transparent cap 24.

Figure 4:
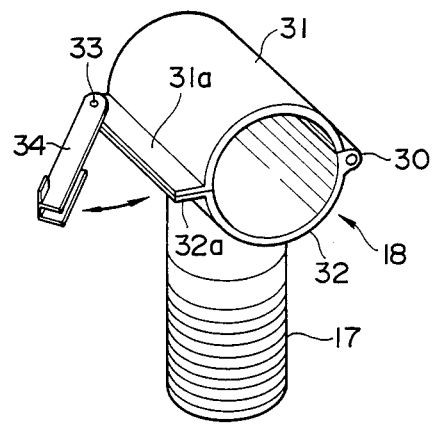
FIG. 4 is a detailed perspective view for explaining an embodiment of the holding member for holding the optical conductor cable.

FIG. 4 is a perspective view showing an embodiment of the holding member (supporter) 18 for holding the optical conductor cable 11 shown in FIG. 3. The holding member 18 comprises semi-circular, cylindrical bodies 31 and 32 capable of rotating around a pin-like shaft 30 and a clasping member 34 having a oneside-open, hollow ended rectangular cross-section which is mounted on either one of the flat-plate portions 31a or 32a formed at the end portion of those semi-circular, cylindrical bodies 31 and 32 in such a manner that the clasping member 34 can rotate around a shaft 33. As is well known, both of the semi-circular cylindrical bodies 31 and 32 are opened by rotating them around the hinge shaft 30.

The end portion (the area A shown in FIG. 3) of the optical conductor cable 11 having the connector 32 firmly fixed thereto, as mentioned above, is inserted into the cylindrical portion formed with those semi-circular cylindrical bodies 31 and 32. And then, those bodies 31 and 32 are closed and the clasping member 34 is rotated around the pin 33, and thereby both of the respective flat-plate portions 31a and 32a, of the afore-mentioned semi-circular cylindrical bodies 31 and 32, are nippingly held by the oneside-open hollow rectangular portion of the clasping member 34. In such a way, the tip end portion of the optical conductor cable 11 can be detachably supported by the supporter 18.

Figure 5:
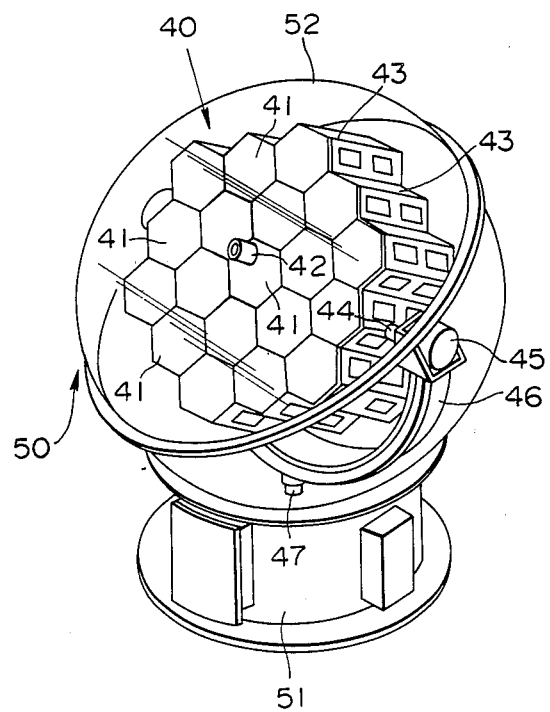
FIG. 5 is a perspective view for explaining an embodiment of a sun ray collecting device used in the present invention.

FIG. 5 is an entire perspective view showing an embodiment of a sun ray collecting device for guiding the sun's rays into the afore-mentioned optical conductor cable 11. In FIG. 5, 50 is a capsule, 51 is a cylindrical (foundation), and 52 is a transparent dome-shaped head portion. The capsule 50 for use in the sun ray collecting device is constructed of a fundamental body portion 51 and a head portion 52. As shown in FIG. 5, the sun ray collecting device 40 is accommodated in the capsule 50 when the device is being used.

The sun ray collecting device 40 comprises one lens, several lenses or possibly a large number of lenses 41, a sun ray direction sensor 42 for detecting the direction of the sun, a support frame body 43 for unitarily holding the lens 41 and a sensor 42, a first-revolution shaft 44 for rotating the support frame body 43, a first-motor 45 for rotating the first-revolution shaft 44, a support arm 46 for supporting the lens 41, the sensor 42, the support frame body 43, the first revolution shaft 44, and the first motor 45, a second revolution shaft 47 installed so as to intersect the first revolution shaft 44 perpendicularly thereto, and a second motor not shown in FIG. 5 for rotating the second revolution shaft 47.

The direction of the sun is detected by means of a sun ray direction sensor 42 and its detection signal controls the first and second motors so as to always direct the lens 41 toward the sun, and the sun's rays focused by the lens 41 are guided into the optical conductor cable, not shown in FIG. 5, the light-receiving end of which is installed at the focal position of the lens 41. The light-receiving end of the optical conductor cable 11 shown in FIG. 2 is not shown in FIG. 5. The guided light rays are transmitted through the optical conductor cable onto an optional desired place.

Concerning the above-mentioned sun ray collecting device, several types of devices have been proposed heretofore by the inventor. They are devices respectively having a lens or several lenses (2 to 4 lenses) or a large number of lenses (as for instance 7, 19, 61, 196 or as many as 1600 lenses) in accordance with the purpose of its use.

Figure 6:
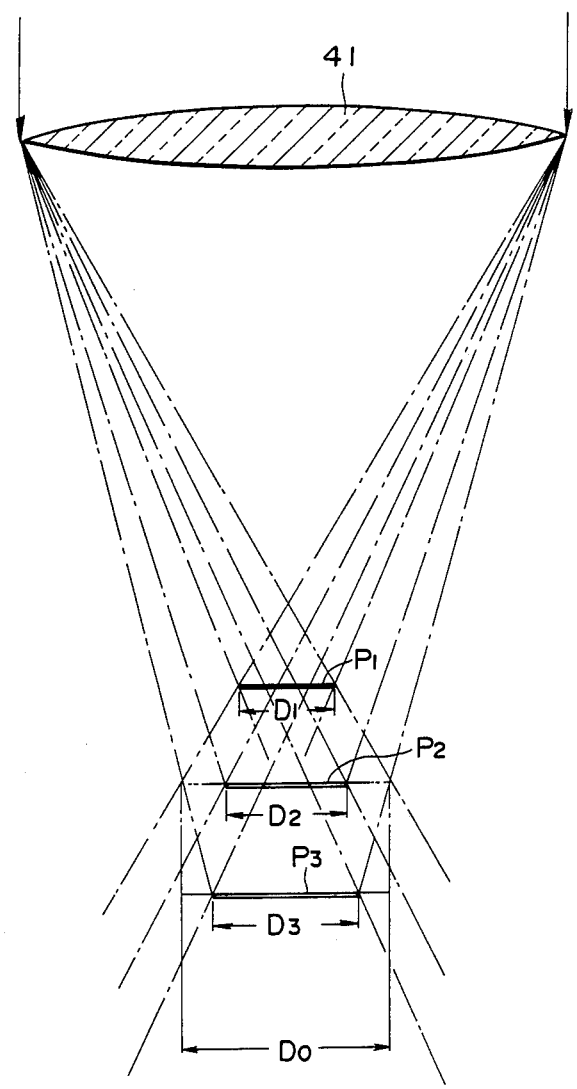
FIG. 6 is a view for explaining a device for guiding the sun's rays into an optical conductor cable.

FIG. 6 is a detailed view for explaining the guiding of light rays that correspond to the visible light ray components of the sun into an optical conductor cable 11. In FIG. 6, 41 is a lens system consisting of a Fresnel lens or the like, and the sun's rays focused by the lens system 41 are guided into an optical conductor cable as mentioned before. In the case of focusing the sun's rays by use of a lens system, the solar image has a central portion consisting of almost white-colored light rays and a circumferential portion containing therein a large amount of light ray components consisting of the wave lengths corresponding to the focal position of the lens system.

Namely, in the case of focusing the sun's rays by the use of the lens system, the position of the lens system and the size of the solar image will vary in accordance with the wave length of the light rays. For instance, the light rays of the color blue, having a short wave length, make a solar image of diameter $D_1$ at position $P_1$. Furthermore, the light rays of the color green make a solar image of diameter $D_2$ at position $P_2$, and the light rays of the color red make a solar image of diameter $D_3$ at position $P_3$.

Consequently, as shown in FIG. 6, when the light-receiving end-surface of the optical conductor cable is put at position $P_1$, it is possible to collect the sun's rays containing plenty of the blue color component at the circumferential portion thereof. When the light-receiving end-surface of the optical conductor cable is put at position $P_2$, it is possible to collect the sun's rays containing plenty of light rays of the green color component at the circumferential portion thereof. When the same is put at position $P_3$, it is possible to collect the sun's rays containing plenty of light rays of the red color component at the circumferential portion thereof. In each case, the diameter of the optical conductor cable is determined by the light ray components to be collected. For instance, the diameters thereof are $D_1$, $D_2$ and $D_3$, respectively, depending on the colors of the light rays to be stressed; i.e. the blue, green and red colors. In such a way, the consumed amount of the optical conductor cable can be reduced, and thereby the sun's rays containing therein plenty of light ray components of the desired color can be collected most effectively. And further, as shown in FIG. 6, if the diameter of the light-receiving end-surface of the optical conductor cable is enlarged to $D_0$, it may be possible to collect visible light rays containing therein all of the wave length components.

As is apparent from the foregoing description, according to the present invention, it may be possible to provide a light ray radiation stand which is low-cost; which is capable of being easily transported around; which doesn't need much space, and which can radiate the light rays in an optional desired direction and thereby can be used very readily.

What is claimed is:

1. A light ray radiation device for holding an optical conductor comprising an upright foundation stand which is generally vertically disposed when in use, said stand having two elongated members longitudinally slidable one within the other to thereby provide for height adjustment of the stand, said stand having an upper end portion, elongated deformable flexible conduit means extending from said upper end portion, said conduit means having outer ends, optical cable holding means mounted on said outer ends for holding an optical cable such that said flexible conduit means enable said optical cable to be moved to various positions so that light rays transmitted through said optical cable can be directed in different directions, said holding means comprising two semi-cylindrical bodies each having a semi-circular cross-sectional configuration and each having a longitudinal extending axis at the center of the respective semi-circular cross-sections, each of said bodies having elongated lateral edge portions extending generally parallel to the respective longitudinal axis, and hinge means pivotably connecting said two lateral edge portions of said two bodies such that said two bodies are pivotable to a closed position wherein said two lateral edge portions abut one another and said two bodies cooperate to define a closed cylinder for holding said optical cable.

2. A light ray radiation device for holding an optical conductor comprising an upright foundation stand which is generally vertically disposed when in use, said stand having an upper end portion, elongated deformable flexible conduit means extending from said upper end portion, said conduit means having outer ends, optical conductor holding means mounted on said outer ends for holding an optical conductor means such that said flexible conduit means enable said optical conductor means to be moved to various positions so that light rays transmitted through said optical conductor means can be directed in different directions, said holding means comprising two semi-cylindrical bodies each having a semi-circular cross-sectional configuration and each having a longitudinal extending axis at the center of the respective semi-circular cross-sectional configuration, each of said bodies having first and second elongated lateral edge portions extending generally parallel to the respective longitudinal axis, hinge means pivotably connecting the two first lateral edge portions of said two bodies such that said two bodies are pivotable to a closed position wherein the two second lateral edge portions abut one another and said two bodies cooperate to define a closed cylinder, said two bodies being pivotal to an open position wherein the two second lateral edge portions are spaced from one another, and clamping means on the two second lateral edge portions for holding said two second lateral edge portions together in a clamped position when said two second lateral edge portions are in said abutting position to thereby clamp said two bodies in said closed position, said two bodies when in said open position receiving said optical conductor means such that the latter is subsequently clamped between said two bodies when the latter are pivoted from said open to said closed position.

3. A light ray radiation stand according to claim 2, wherein said two second edge portions are generally flat and extend generally in a diametric direction when said two bodies are in said closed position, said holding means further comprising a pivotal clamp arm and second pivotal means pivotably mounting said clamp arm on one of said two second edge portions, said clamp arm being pivotable about an axis which is generally perpendicular to said one of said two second flat edge portions, said clamp arm having a generally U-shaped end section, said clamp arm being pivotable to a closed position in which said U-shaped end section receives said two abutting second edge portions of said bodies when the latter are in said closed position to thereby hold and clamp said two abutting second edge portions together.

4. A light ray radiation stand according to claim 3, wherein said optical conductor means has a cylindrical portion which is received and retained between said two bodies when the latter are in said closed position.

5. The combination comprising an upright light ray radiation stand which is generally vertically disposed when in use, said stand having an upper end portion, elongated deformable flexible conduit means extending from said upper end portion, said conduit means having outer ends, holding means mounted on said outer ends, an optical conductor means held by said holding means such that said flexible conduit means enable said optical conductor means to be moved to various positions so that light rays transmitted through said optical conductor means can be directed in different directions, said optical conductor means comprising an elongated optical cable having a light-emitting end section having a light-emitting terminating end, an external cover disposed about at least a longitudinal portion of said light-emitting end section, a connector connected to said cover and extending longitudinally beyond said light-emitting terminating end, a transparent cap mounted on said connector and having an end part spaced from said terminating end, a heat-reflective filter, and mounting means mounting said heat-reflective filter on said transparent cap to dispose said heat-reflective filter in said space between said end part of said transparent cap and said terminating end such that light rays emitted from said terminating end are radiated through said heat-reflective filter and said end part of said transparent cap.

6. The combination comprising an upright light ray radiation stand which is generally vertically disposed when in use, said stand having an upper end portion, elongated deformable flexible conduit means having outer ends, holding means mounted on said outer ends, an optical conductor means held by said holding means such that said flexible conduit means enable said optical conductor means to be moved to various positions so that light rays transmitted through said optical conductor means can be directed in different directions, said holding means comprising two semi-cylindrical bodies each having a semi-circular cross-sectional configuration and each having a longitudinal extending axis at the center of the respective semi-circular cross-sectional configuration, each of said bodies having first and second elongated lateral edge portions extending generally parallel to the respective longitudinal axis, hinge means pivotably connecting the two first lateral edge portions of said two bodies such that said two bodies are pivotable to a closed position wherein the two second lateral edge portions abut one another and said two bodies cooperate to define a closed cylinder, said two bodies being pivotal to an open position wherein the two second lateral edge portions are spaced from one another, clamping means on the two second lateral edge portions for holding said two second edge portions together in a clamped position when said two second edge portions are in said abutting position to thereby clamp said two bodies in said closed position, said two bodies when in said open position receiving said optical conductor cable such that the latter is subsequently clamped between said two bodies when the latter are pivoted from said open to said closed position, said optical conductor means comprising an elongated optical cable having a light-emitting end section having a light-emitting terminating end, an external cover disposed about at least a longitudinal portion of said light-emitting end section, a connector connected to said cover and extending longitudinally beyond said light-emitting terminating end, and a transparent cap mounted on said connector and having an end part spaced from said terminating end such that light rays emitted from said terminating end are radiated through said end part of said transparent cap.

7. The combination as set forth in claim 6 further comprising external thread means on said cover, said connector being threaded onto said thread means, and an elongated nut part threaded on said thread means and abutting said connector, said nut part and said connector each having an outer cylindrical portion which is retained between said two bodies when the latter are in said closed position.

* * * * *